US012616775B2

(12) United States Patent
Kasuga et al.

(10) Patent No.: US 12,616,775 B2
(45) Date of Patent: *May 5, 2026

(54) METHOD FOR MANUFACTURING BONE-REGENERATION MATERIAL COMPRISING BIODEGRADABLE FIBERS BY USING ELECTROSPINNING METHOD

(71) Applicants: NATIONAL UNIVERSITY CORPORATION NAGOYA INSTITUTE OF TECHNOLOGY, Nagoya (JP); ORTHOREBIRTH CO., LTD., Yokohama (JP)

(72) Inventors: Toshihiro Kasuga, Nagoya (JP); Yasutoshi Nishikawa, Yokohama (JP)

(73) Assignees: NATIONAL UNIVERSITY CORPORATION NAGOYA INSTITUTE OF TECHNOLOGY, Nagoya (JP); ORTHOREBIRTH CO., LTD., Yokohama (JP)

( * ) Notice: Subject to any disclaimer, the term of this patent is extended or adjusted under 35 U.S.C. 154(b) by 280 days.

This patent is subject to a terminal disclaimer.

(21) Appl. No.: 18/630,735

(22) Filed: Apr. 9, 2024

(65) Prior Publication Data
US 2024/0252714 A1 Aug. 1, 2024

Related U.S. Application Data

(63) Continuation of application No. 16/840,309, filed on Apr. 3, 2020, now Pat. No. 11,969,521, which is a
(Continued)

(30) Foreign Application Priority Data

Apr. 28, 2016 (JP) .................................. 2016-091118

(51) Int. Cl.
A61L 27/44 (2006.01)
A61F 2/28 (2006.01)
(Continued)

(52) U.S. Cl.
CPC ............... *A61L 27/18* (2013.01); *A61L 27/12* (2013.01); *A61L 27/44* (2013.01); *A61L 27/46* (2013.01);
(Continued)

(58) Field of Classification Search
CPC ........ A61L 27/425; A61L 27/44; A61L 27/46; A61L 27/58; A61L 2430/02; A61L 27/18; A61L 27/12; A61L 27/54; A61L 27/56; A61L 2300/412; A61L 2400/06; A61L 2400/12; A61F 2/28; B29B 7/845; B29B 2013/005; C08J 3/201; C08K 2003/325; D01D 1/02; D01D 5/0038; D01D 5/0046; D01D 5/08; D01D 5/003; D01F 1/02;
(Continued)

*Primary Examiner* — Ernst V Arnold
(74) *Attorney, Agent, or Firm* — Liang Legal Group, PLLC; T. Chyau Liang

(57) ABSTRACT

A bone-regeneration material comprising a biodegradable fiber produced using an electrospinning process, wherein the biodegradable fiber comprises 30 to 50 wt % of PLLGA resin and 70 to 50 wt % of β-TCP fine particles substantially uniformly dispersed in the PLLGA resin without forming aggregates, wherein the β-TCP fine particles are not chemically bonded to the PLLGA resin, and surroundings of the β-TCP fine particles are covered by the PLLGA resin so that
(Continued)

the β-TCP fine particles are not separated from the biodegradable fiber during a formation of the fiber, and wherein the bone-regeneration material is sterilized by using radiation sterilization with gamma ray.

6 Claims, 14 Drawing Sheets

Related U.S. Application Data continuation of application No. 15/773,554, filed as application No. PCT/JP2017/016931 on Apr. 28, 2017, now Pat. No. 10,646,616.

(51) Int. Cl.

| | |
|---|---|
| *A61L 27/12* | (2006.01) |
| *A61L 27/18* | (2006.01) |
| *A61L 27/46* | (2006.01) |
| *A61L 27/54* | (2006.01) |
| *A61L 27/56* | (2006.01) |
| *A61L 27/58* | (2006.01) |
| *B29B 7/84* | (2006.01) |
| *C08J 3/20* | (2006.01) |
| *D01D 1/02* | (2006.01) |
| *D01D 5/00* | (2006.01) |
| *D01D 5/08* | (2006.01) |
| *D01F 1/02* | (2006.01) |
| *D01F 1/10* | (2006.01) |
| *D01F 6/62* | (2006.01) |
| *B29B 13/00* | (2006.01) |
| *C08K 3/32* | (2006.01) |

(52) U.S. Cl.
CPC ............... *A61L 27/54* (2013.01); *A61L 27/56* (2013.01); *A61L 27/58* (2013.01); *B29B 7/845* (2013.01); *C08J 3/201* (2013.01); *D01D 1/02* (2013.01); *D01D 5/0038* (2013.01); *D01D 5/0046* (2013.01); *D01D 5/08* (2013.01); *D01F 1/02* (2013.01); *D01F 1/10* (2013.01); *D01F 6/62* (2013.01); *D01F 6/625* (2013.01); *A61L 2300/412* (2013.01); *A61L 2400/06* (2013.01); *A61L 2400/12* (2013.01); *A61L 2430/02* (2013.01); *B29B 2013/005* (2013.01); *C08K 2003/325* (2013.01); *D10B 2331/041* (2013.01); *D10B 2401/12* (2013.01); *D10B 2509/00* (2013.01); *D10B 2509/06* (2013.01)

(58) Field of Classification Search
CPC ... D01F 1/10; D01F 6/62; D01F 6/625; D10B 2331/041; D10B 2401/12; D10B 2509/00; D10B 2509/06
See application file for complete search history.

| Mixing ratio of resin and β-TCP | Temperature | Viscosity | Time for Kneading | Results of Kneading | ES results |
|---|---|---|---|---|---|
| (1) PLLGA/β-TCP : 30/70 | 185°C | Lower than working viscosity range | Polymer alone was kneaded for 3 and half minutes and then powder was mixed and the mixture was kneaded for 11 minutes | A part of PLLGA was stuck to wall surface of kneader and remaining part of β-TCP powder remained unmixed with PLLGA. | Not conducted |
| (2) PLLGA/β-TCP : 30/70 | 165°C | Within working viscosity range | Polymer alone was kneaded for 3 and half minutes and then powder was mixed and the mixture was kneaded for 11 minutes | All of provided β-TCP powder was mixed with and dispersed in PLLGA and no powder was observed to remain. | Fiber was produced stably by ES at a 8% concentration of PLLGA in chloroform |
| (3) PLLGA/β-TCP : 30/70 | 115°C | Higher than working viscosity range | Polymer alone was kneaded for 3 and half minutes and then powder was mixed and the mixture was kneaded for 11 minutes | PLLGA was not softened enough and β-TCP was not mixed with PLLGA | Not conducted |
| (4) PLLGA/β-TCP : 50/50 | 165°C | Within working viscosity range | Polymer alone was kneaded for 3 and half minutes and then powder was mixed and the mixture was kneaded for 11 minutes | All powder of β-TCP was successfully mixed with and dispersed in PLLGA. Powder was not observed to remain after kneading. | Fiber was produced stably by ES at a 8% concentration of PLLGA in chloroform |

Figure 4 (A)

| Mixing ratio of resin and β-TCP | Temperature | Viscosity | Time for kneading | Results of kneading | ES results |
|---|---|---|---|---|---|
| (5) PDLGA/β-TCP : 30/70 | 140°C | Higher than working viscosity range | Polymer alone was kneaded for 3 and half minutes and then powder was mixed and the mixture was kneaded for 11 minutes | PDLGA was not softened enough and β-TCP was not mixed | Not conducted |
| (6) PDLGA/β-TCP : 30/70 | 165°C | Within working viscosity range | Polymer alone was kneaded for 3 and half minutes and then powder was mixed and the mixture was kneaded for 11 minutes | Some PDLGA was attached to blades of the kneader. A slight amount of β-TCP was not mixed and remained. | Not conducted |
| (7) PDLGA/β-TCP : 30/70 | 165°C | Within working viscosity range | Polymer and powder were provided to kneader at the same time and mixed and kneaded for 14 and half minutes | Total amount of provided β-TCP powder was successfully mixed with PDLGA. Powder was not observed to remain after kneading. | Fiber was successfully produced at a 12% concentration of PDLGA in chloroform, but did not become cottonwool-like after drying. |
| (8) PDLGA/β-TCP : 50/50 | 165°C | Within working viscosity range | Polymer alone was kneaded for 3 and half minutes and then powder was mixed and the mixture was kneaded for 11 minutes | Some PDLGA was attached to blades of the kneader. A slight amount of β-TCP was not mixed and remained. | Not conducted |
| (9) PDLGA/β-TCP : 50/50 | 185°C | Within working viscosity range | Polymer and powder were provided to kneader at the same time and mixed and kneaded for 14 and half minutes | All powder of provided β-TCP was successfully mixed with total amount of PDLGA. Powder was not observed to remain after kneading. | Not conducted |

Figure 4 (B)

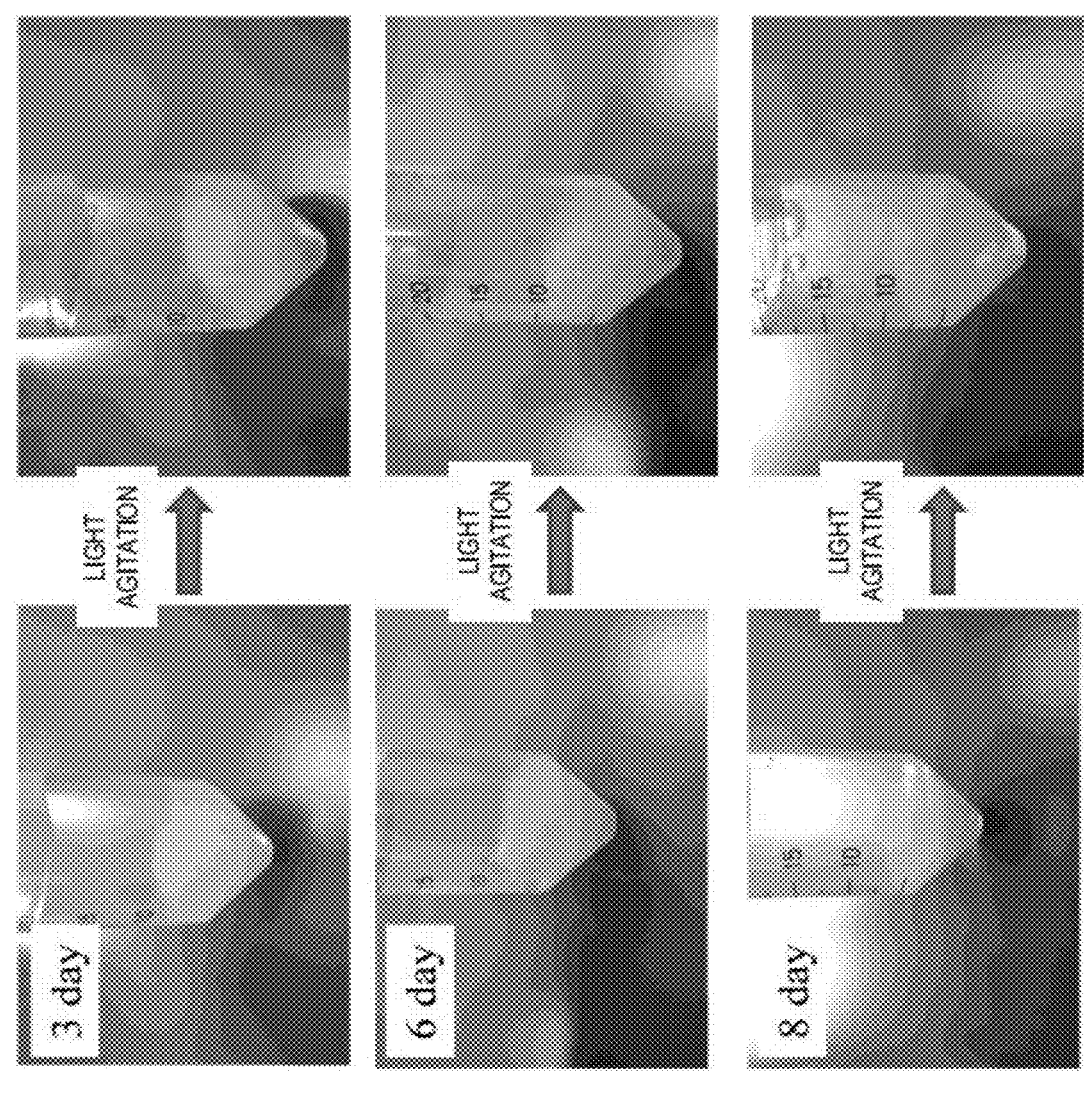
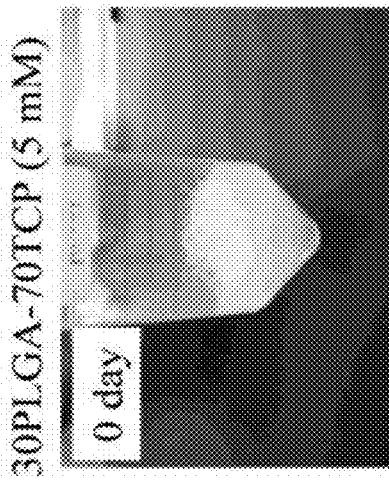
Figure 5 (A)

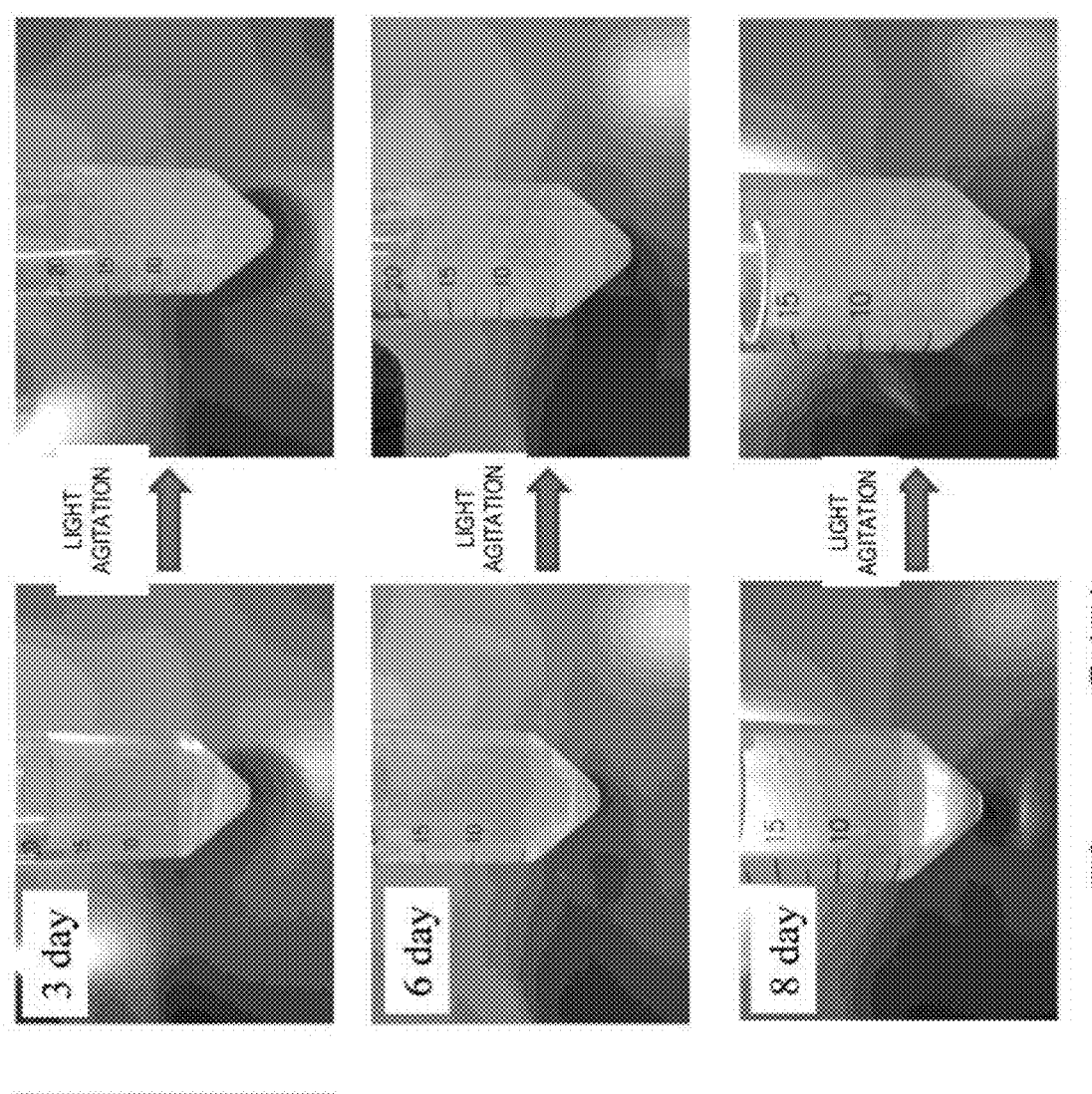
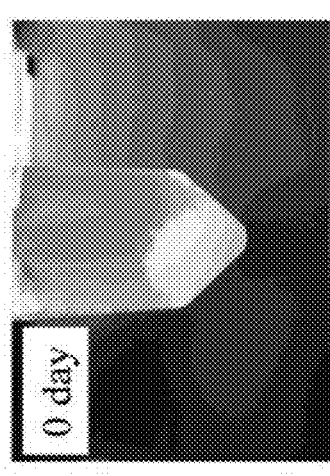
Figure 5 (E)

| Melting enthalpy of crystal with infinite thickness | |
| --- | --- |
| PLLA | 93.6 |
| PGA | 191.2 |
| PLGA8515 (Theo. value) | 108.24 |

| | Glass transition temperature | Melting point | Heat of fusion [J/g] | Crystallinity |
| --- | --- | --- | --- | --- |
| (1) 30PLLGA-70TCP | 74.2 | 180.5 | 3.626 | 3.3 |
| (2) 40PLLGA-60TCP | 75.4 | 160.8 | 4.798 | 4.4 |
| (3) 50PLLGA-50TCP | 69.2 | 158.7 | 7.050 | 6.5 |
| (4) 100PLLGA | 73.3 | 162.1 | 14.249 | 13.2 |
| (5) 30PDLGA-70TCP | 66.2 | NA | NA | NA |
| (6) 50PDLGA-50TCP | 66.0 | NA | NA | NA |

Crystallinity was calculated by the following equation.

Crystallinity (%) = (measured enthalpy/melting enthalpy of crystal with infinite thickness*) × 100

Melting enthalpy of crystal with infinite thickness of PLGA was calculated to be 108.24 J/g from the literature values for PLLA and PGA with composition ration of 85:15.

In PLGA type containing D isomer, crystallinity was indicated as NA because no peak was found other than the peak of glass transition.

Figure 6 (B)

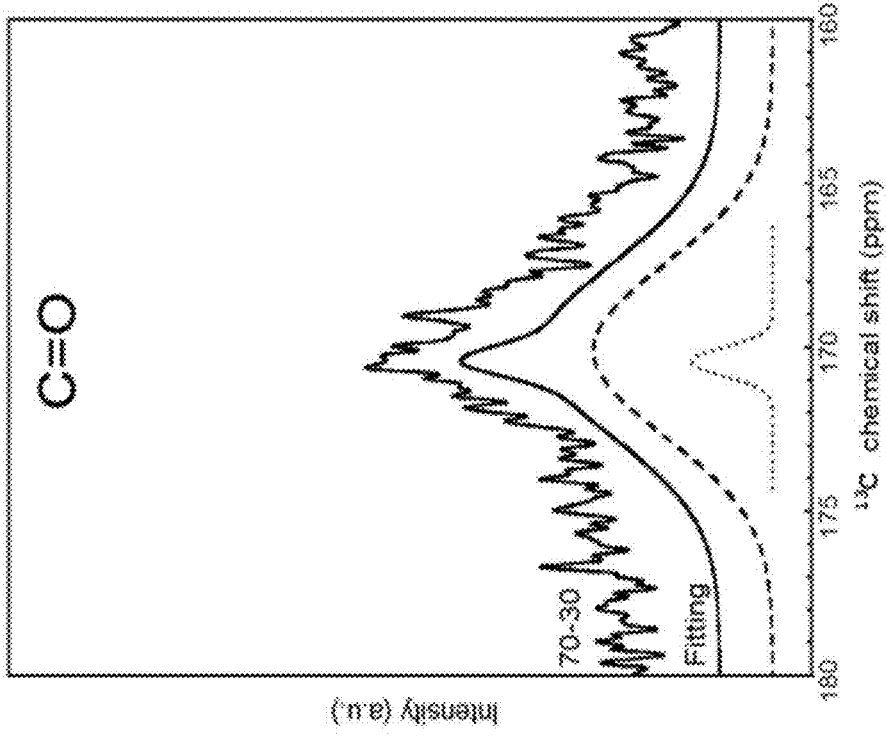
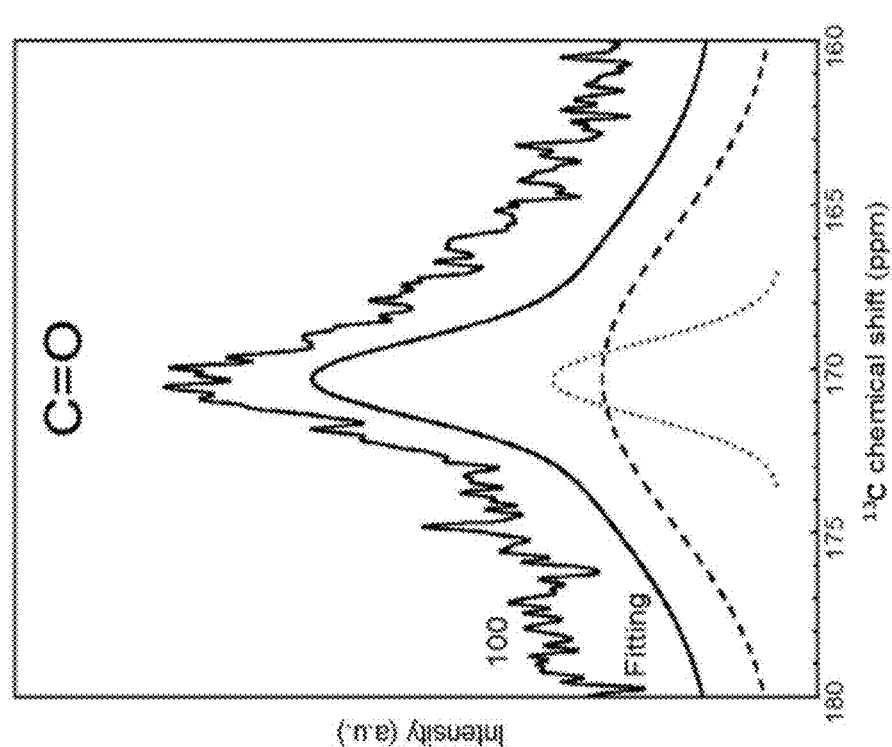
$^{13}$C CP/MAS-NMR SPECTRA OF PLGA (100) AND TCP/PLGA (70-30)
Figure 7 (B)

β-TCP (RAW MATERIAL)

METHOD FOR MANUFACTURING BONE-REGENERATION MATERIAL COMPRISING BIODEGRADABLE FIBERS BY USING ELECTROSPINNING METHOD

CROSS REFERENCE TOP RELATED APPLICATIONS

This is a continuation application of U.S. application Ser. No. 16/840,309, filed on Apr. 3, 2020, which is a continuation of U.S. application Ser. No. 15/773,554, filed on May 3, 2018, which is a national stage application of PCT/JP2017/016931, filed on Apr. 28, 2017, which claims the priority of Japanese Application No. 2016-091118, filed on Apr. 28, 2016. The disclosures of these prior applications are incorporated by reference in their entirety.

TECHNICAL FIELD

This invention relates to a method for producing a bone-regeneration material comprising biodegradable fibers by using an electrospinning method.

BACKGROUND

Methods being practiced in the field of bone regeneration therapy involve implanting into a bone defect part a bone regeneration material prepared by adding a bone morphogenetic factor into a matrix resin made of a biodegradable resin such as polylactic acid (PLA), polylactic acid-glycolic acid copolymer (PLGA) are performed. Since, after the implantation of the bone regeneration material in the body, the material is in contact with body fluid and degraded and thereby the bone morphogenetic factor contained in the material is slowly release and also the material is absorbed and removed by the body over time, an effective bone formation is achieved with a little burden on the patient.

The requirement for a bone-regeneration material to exhibit an osteogenic activity when it is implanted in the body is that a matrix resin therein serves as a scaffold and is a resin on which a bone morphogenetic factor can be supported. As a bone morphogenetic factor, calcium phosphate, in particular, β phase tricalcium phosphate (β-TCP) is preferably used since it has an excellent osteogenic activity. Since the bone resorption and/or replacement by β-TCP requires several months, it is desirable that the matrix resin comes in contact with body fluid and hydrolyzed early to start controlled release of calcium phosphate, continues the controlled release for a certain period of time, and then is rapidly degraded and absorbed to be disappeared.

Recently, biodegradable fiber containing a bone morphogenetic factor has been actively used as a bone-regeneration material, and electrospinning processes are used as a method for producing such biodegradable fiber. In the electrospinning process, a spinning solution is ejected as a thin fiber from a nozzle and pulled by the electrostatic attraction in the electric field to be deposited on a collector. Therefore, it is an important object to prepare a spinning solution that is available for such spinning.

In vivo and in vitro evaluation of flexible, cottonwool-like nanocomposite as bone substitute material for complex defects Acta Biomaterialia 5 2009 discloses formation of fibers in a cottonwool-like form using a low temperature electrospinning process from a spinning solution. The spinning solution is prepared by adding PLGA to a solvent and dissolved in the solvent in which amorphous TCP fine particles are dispersed. The method of the document involves preparing a spinning solution (the weight ratio of PLGA/TCP is 60/40) for electrospinning by dispersing TCP particles by sonication in chloroform, providing PLGA to and dissolved in the chloroform, and stirring the mixture.

The inventors of the present invention proposed a method of preparing a spinning solution in which a composite is prepared by adding silicon-releasing calcium carbonate particles together with calcium phosphate particles to a PLA melt and mixing and kneading and cooling and solidifying the mixture. The composite is then dissolved by using a solvent to produce a spinning solution (Japanese patent No. 5855783). According to this method, a spinning solution can be produced by incorporating 50% by weight or more inorganic particles into a polylactic resin. However, since the degradation and absorption of PLA in the body is slow, the possibility has been pointed out that it prevents inorganic fine particles from early exhibition of osteogenic potential. Moreover, there is the problem that when fine particle powder with a particle size of about 1 to 4μ is provided to and kneaded with a solution which has been heated to above the melting point of the PLA resin and melted, the fine particles are aggregated and fail to be completely dispersed in the resin by kneading.

CITATION LIST

Patent Literature

Patent Literature 1: Japanese Patent No. 5855783

Non Patent Literature

Non Patent Literature 1: In vivo and in vitro evaluation of flexible, cottonwool-like nanocomposite as bone substitute material for complex defects, Acta Biomaterialia 5, 2009, 1775-1784, Stark et al., University of Zurich.

SUMMARY OF INVENTION

Problem to be Solved by the Invention

PLGA is superior to PLA in that it is hydrolyzed at a high speed and the resin is degraded and absorbed when implanted in the living body allowing controlled release of a bone morphogenetic factor early without remaining in the body for a long period of time and thus widely used as resin for a scaffold of bone regeneration material. However, since PLGA is an amorphous resin, it is a material that is more difficult in forming and workability of fiber for producing biodegradable fiber using an electrospinning process than PLA.

It is desirable that calcium phosphate fine particles contain a bone morphogenetic factor as much as possible for exhibiting the osteogenic activity. However, the spinning by electrospinning tends to be difficult when the spinning solution contains a large amount of particles.

Under the situation as described above, there have been desired a novel method for effectively producing a bone-regeneration material comprising biodegradable fiber including PLGA and a large amount of calcium phosphate particles contained therein by electrospinning at a level applicable on a commercial basis and a novel bone-regeneration material produced by the method.

Means for Solving the Problem

The present invention relates to a method for commercially producing a biodegradable fiber made of a PLGA resin containing a large amount of calcium phosphate particles, in particular β-TCP fine particles with a small particle size by using an electrospinning process.

The present invention further relates to a biodegradable fiber made of a PLGA resin containing calcium phosphate particles, wherein the biodegradable fiber is produced by using an electrospinning process.

The present invention further relates to a method for producing a spinning solution for electrospinning to be used in the method for production described above.

The present invention further relates to a bone regeneration material in a nonwoven fabric or cottonwool-like form, including a biodegradable fiber produced by an electrospinning process and a method for production thereof.

One embodiment of the present invention is a method for producing a bone-regeneration material including biodegradable fiber using an electrospinning process, comprising:

providing a PLGA resin to a kneader and heating the PLGA resin to soften the PLGA resin to a viscosity of 102 to 107 Pa·s;

mixing powder of calcium phosphate fine particles with the softened PLGA resin by providing the powder into the kneader while rotating the blade of the kneader;

rotating the blade of the kneader with continuous force under the heating to knead the mixture so that thermal and mechanical energy is applied to the mixture to crush aggregates of the calcium phosphate fine particles, and thereby prepare a composite of the PLGA resin and the calcium phosphate fine particles dispersed therein;

cooling and solidifying the composite;

dissolving the composite with a solvent, and stirring for a predetermined time to prepare a spinning solution in which the PLGA resin is completely dissolved in the solvent and the calcium phosphate fine particles are dispersed without aggregation in the solvent in which the PLGA resin is dissolved; and charging the spinning solution into a syringe of an electrospinning apparatus and applying high voltage to produce a biodegradable fiber in which the calcium phosphate fine particles are dispersed substantially uniformly in the biodegradable fiber.

Preferably, the calcium phosphate fine particles are β-TCP fine particles.

Preferably, the PLGA resin is softened to a viscosity of 103.2 to 103.6 Pa·s in the kneader.

One embodiment of the present invention is a bone-regeneration material including biodegradable fiber produced by using an electrospinning process, wherein the biodegradable fiber includes about 30 to 60% by weight of PLGA resin and about 70 to 40% by weight of calcium phosphate fine particles;

the biodegradable fiber is produced by providing a predetermined amount of a PLGA resin to a heating kneader and heating the PLGA resin at a predetermined temperature to soften the PLGA resin to a viscosity of $10^2$ to $10^7$ Pa·s; then providing the calcium phosphate fine particles to the kneader and applying thermal and mechanical energy to the mixture to crush aggregates of the β-TCP fine particles, and thereby prepare a composite of the PLGA resin and the calcium phosphate fine particles substantially uniformly dispersed in the PLGA resin, cooling and solidifying the composite, and then electrospinning the spinning solution prepared by dissolving the composite by using a solvent; wherein calcium ions in the calcium phosphate fine particles are not bonded to carboxyl groups of the PLGA resin.

Preferably, the calcium phosphate fine particles are β-TCP fine particles.

Preferably, the PLGA resin is softened to a viscosity of 103.2 to 103.6 Pa·s in the kneader.

Preferably, the PLGA resin and the calcium phosphate fine particles are provided to the kneader to about 30 to 50% by weight and to about 70 to 50% by weight, respectively, and kneaded.

Preferably, after the PLGA resin is provided to the kneader and heated to be softened to a predetermined viscosity and kneaded for a predetermined time, the powder of calcium phosphate fine particles is provided to the kneaded PLGA resin in the kneader and the PLGA resin and the calcium phosphate fine particles are kneaded in the kneader for a predetermined time at a temperature substantially equivalent to the temperature of the kneading.

Preferably, the calcium phosphate fine particles are β-TCP fine particles.

Preferably, the PLGA resin is a copolymer of PLA containing only the L-isomer of PLA and PGA.

Preferably, the PLGA resin is a copolymer of PLA containing the L-isomer and the D-isomer of PLA in mixture and PGA.

Preferably, the ratio of lactic acid and glycolic acid in the PLGA resin is approximately 85-50:15-50.

Preferably, the outer diameter of the β-TCP particles is 0.5 to 4 μm.

Preferably, the outer diameter of the biodegradable fiber is 10 to 250 μm.

Preferably, a collector of the electrospinning device is filled with ethanol and fiber ejected from a nozzle is deposited in a cottonwool-like form in a liquid ethanol in the collector container.

Preferably, the bone-regeneration material including the biodegradable fiber is in a cottonwool-like form with a bulk density of 0.01 to 0.1 g/cm³.

Preferably, the molecular weight of the PLGA resin is 60000 to 600000.

By using the method for producing a bone regeneration material of the present invention, a bone regeneration material including biodegradable fiber can be commercially produced efficiently by an electrospinning process using PLGA, which is generally more difficult in forming and/or processing than PLA, as a biodegradable resin.

Because the biodegradable fiber that contains a PLGA resin as a biodegradable resin produced by the method for producing a bone regeneration material of the present invention is degraded and absorbed rapidly in the body, it allows early controlled release of β-TCP and promotes the bone formation.

Because the biodegradable fiber produced by using the process of the present invention can be deposited in a cottonwool-like form on a collector of electrospinning apparatus and collected therefrom, it can be suitably used as a bone regeneration material in a cottonwool-like form.

BRIEF DESCRIPTION OF DRAWINGS

FIG. 4(A) illustrates a result of Experiment 1 (PLLGA).

FIG. 4(B) illustrates a result of Experiment 1 (PDLGA).

DETAILED DESCRIPTION OF THE INVENTION

Figure 1:
FIG. 1 is a photograph of general view of a bone regeneration material that is an embodiment of the present invention.

Embodiments of the present invention are described below in detail referring to the drawings.

<PLGA Resin>

For the biodegradable resin of the present invention, PLGA resin is preferably used. In the present invention, PLGA resin widely includes copolymers of lactic acid and glycolic acid. In general, the PLGA resin is amorphous and therefore they have no distinctive melting point, whereas they are softened when heated.

The ratio of lactic acid and glycolic acid in the PLGA resin of the present invention is determined appropriately as needed. It may include 85:15, 75:25, and 50:50.

Figure 6:
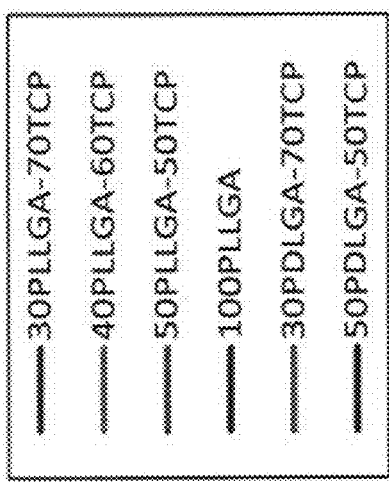
FIG. 6(A) illustrates results of DSC measurement of Samples (1) to (6).
FIG. 6(B) illustrates results of DSC measurement of Samples (1) to (6).

Polylactic acid (PLA) includes poly-L-lactic acid (PLLA), in which only L-form isomer is polymerized, poly-D-lactic acid (PDLA), in which only D-form isomer is polymerized, and PDLLA, in which both L- and D-isomers of lactic acid are present in mixture. PLGA of the present invention may be a copolymer of any of these types of polylactic acid and polyglycolic acid. In the present application, copolymers of PLLA and PGA are referred to as PLLGA and copolymers of PDLA and PGA are referred to as PDLGA. As demonstrated in the results of DSC measurement in FIGS. 6 (1) and (2), PDLGA has no crystallized portion, whereas PLLGA has a crystallized portion.

<β Phase Tricalcium Phosphate>

As the bone morphogenetic factor to be used in the bone-regeneration material of the present invention, fine particles of β phase tricalcium phosphate (β-TCP) are preferably used. Generally known calcium phosphate includes bioabsorbable calcium phosphate such as calcium hydrogenphosphate, octacalcium phosphate, tetracalcium phosphate, tricalcium phosphate, carbonate apatite, and the like.

β-TCP is particularly preferable as a material to be a scaffold for proliferation and differentiation of cells of the osteoblast. Appearance of the β-TCP fine particles is powder. Diameter of the particles of the powder is preferably 0.5 to 4 μm. Since the outer diameter of the fiber composing the bone-regeneration material of the present invention is 10 to 150 μm, the particle diameter is preferably about 4 μm or less. To have the β-TCP particles uniformly distributed with calcium phosphate particles, which are both kneaded with the β-TCP particles, outer diameter of the β-TCP particles is preferably about 0.5 to 4 μm, which is equivalent to that of calcium phosphate particles.

Figure 8:
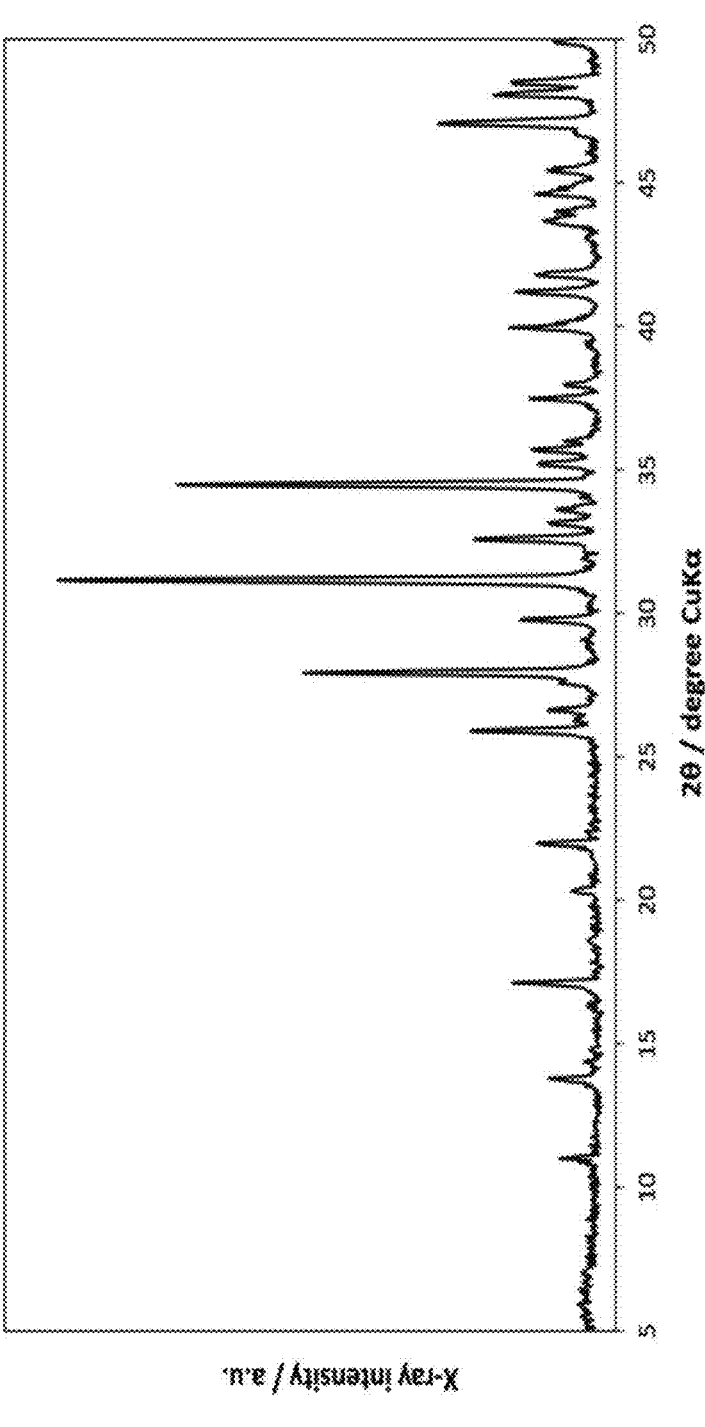
FIG. 8 illustrates results of XRD measurement of β-TCP to be used in the present invention.

If the calcium phosphate of the present invention is β-TCP that contains almost no amorphous phase, it is considered that the calcium phosphate is not bound to the polymer molecules by the kneading with the biodegradable resin. FIG. 8 illustrates the result of the XRD measurement of the β-TCP to be used in the present invention. The presence of distinctive peaks indicates that β-TCP is crystalline.

<Production of Spinning Solution>

(1) Preparation of Composite by Kneading

Pellets of PLGA resin are provided to a kneader and heated to the range of working temperature to soften the PLGA resin to a range of working viscosity, that is, a viscosity of 102 to $10^7$ Pa·s or more preferably $10^{3.2}$ to $10^{3.6}$ Pa·s. Then, powder of calcium phosphate fine particles are provided to the kneader, mixed with a biodegradable resin, and kneaded for a certain period of time to prepare a composite of calcium phosphate particles and biodegradable resin.

Preferably, weight percentages of the PLGA resin and the calcium phosphate fine particles in the composite are about 30 to 60% by weight of PLGA and about 70 to 40% by weight of calcium phosphate. More preferably, the PLGA resin is about 30 to 50% by weight and the calcium phosphate fine particles are about 70 to 50% by weight. Furthermore preferably, the PLGA resin is about 30% by weight and the calcium phosphate fine particles are about 70% by weight. Since it is difficult to control the weight percentages of the PLGA resin and the calcium phosphate accurately to the level less than 10% in the present invention, the numerical value ranges described above should be construed to include the ranges plus and minus 5%.

In order to increase the osteogenic activity of a bone regeneration material, content of calcium phosphate should be increased as much as possible. However, if the amount of calcium phosphate is increased to a percentage substantially exceeding 70% by weight, for example to 80% by weight, it becomes difficult to electrospin a fiber from the spinning solution prepared from such composite.

TCP fine particles tend to form aggregates when they are mixed with a softened PLGA resin. However, by applying thermal and mechanical energy to the mixture of TCP fine particles and PLGA having a viscosity of $10^2$ to $10^7$ Pa·s or more preferably $10^{3.2}$ to $10^{3.6}$ Pa·s and kneading the mixture in a kneader for a certain period of time, aggregates of TCP fine particles are physically crushed so that polymer is allowed to permeate between particles and it becomes possible to create a state where calcium phosphate fine particles are substantially uniformly dispersed in the PLGA resin. The term applying thermal and mechanical energy refers to kneading resin with a force in a state where the resin is softened by being heated to have a high viscosity. By kneading the resin in a state where the resin has high viscosity, aggregates of the calcium phosphate fine particles contained in the resin are physically crushed.

A suitable kneader to be used in the present invention is a type of kneader suitable for kneading materials with high viscosity or involving crushing solids. For effectively crushing calcium phosphate fine particles in a biodegradable resin with high viscosity, for example, a PBV model of kneader in which materials are shear-mixed with 2 pieces of screw-shaped blades and a wall surface by cutting non-uniform motion of the blades to be particularly strongly crushed and kneaded is suitable. Moreover, a kneader equipped with a cartridge heater or the like and capable of heating to the melting point of the resin in a short period of time is desirable.

In order to apply thermal and mechanical energy to calcium phosphate particles in a kneader, PLGA softened by heating is required to have a viscosity higher than a certain level. The range (working temperature range) of heating temperature to have the PLGA resin within a suitable working viscosity range ($10^2$ to $10^7$ Pa·s, or more preferably $10^{3.2}$ to $10^{3.6}$ Pa·s) varies depending on the kind of the PLGA resin. For PLLGA (85:15), a temperature around 160° C. is preferable. At a heating temperature (for example 140° C. for PLLGA) lower than such temperatures, a stronger force is required for kneading in a kneader, resulting in lower efficiency of kneading.

If the heating temperature is further increased (for example, increasing the temperature from around 160° ° C. for PLLGA to 190° C. or more), viscosity of the PLGA resin is decreased so that the polymer is made to be in a liquid phase state. As a result, it would become difficult to apply mechanical energy by kneading the resin to crush aggregates of calcium phosphate fine particles. As a result, it would become difficult to uniformly disperse β-TCP fine particles in the PLGA resin.

In the present invention, PLGA resin may be provided earlier to a kneader and heated and then calcium phosphate fine particles are provided and kneaded, or a PLGA resin and calcium phosphate fine particles may be provided to a kneader at the same time and mixed and kneaded, or a mixture obtained by mixing a PLGA and calcium phosphate fine particles may be provided to a kneader and kneaded. If crystallinity of PLGA is low, viscosity of the polymer becomes low when heated. Therefore, thermal and mechanical energy can be more easily applied to the mixture if calcium phosphate fine particles and PLGA are provided to a kneader at the same time and kneaded therein without heating the PLGA resin prior to entering the calcium phosphate fine particles into the kneader.

Figure 7:
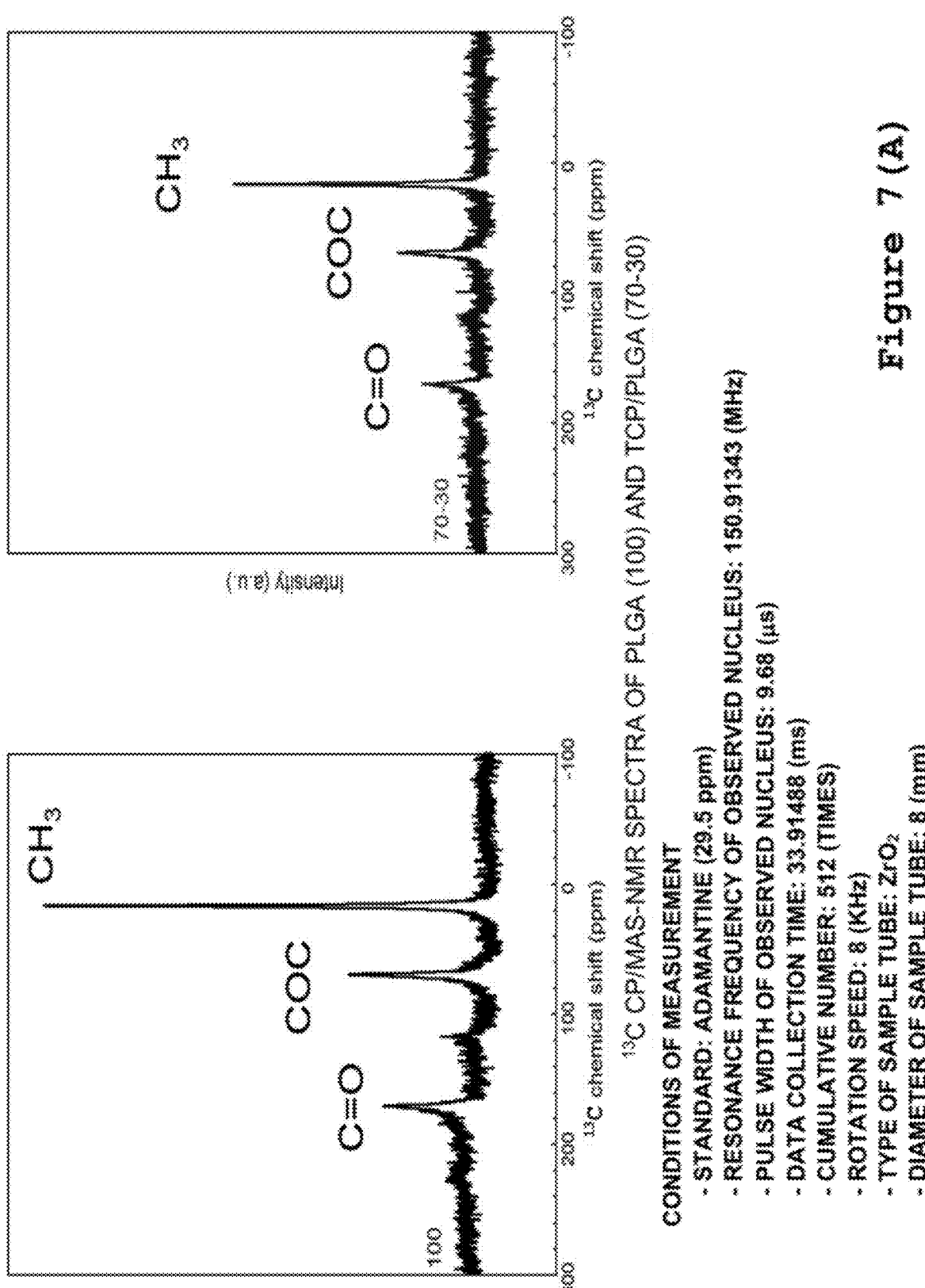
FIG. 7(A) illustrates results of NMR measurement of Samples (1) and (4).
FIG. 7(B) illustrates results of NMR measurement of Samples (1) and (4).

Relations that may be created between PLGA resin and calcium phosphate fine particles by kneading the mixture is not clear at molecular level. Solid nuclear magnetic resonance (NMR) measurements of samples of the biodegradable fiber prepared by the method of the present invention indicated that carboxyl groups of the PLGA resin are not bonded to calcium ions of β-TCP. FIGS. 7 (1) and (2) shows the result of the NMR measurement.

It is considered that if β-TCP is not amorphous phase, there is no chemical bond with the PLGA resin. If there is a reaction between the calcium phosphate particles and the biodegradable resin matrix to generate a bonding binding at the interface, that may cause a concern during the examination of pharmaceutical administration as to whether there is an effect on the living body when they are used as a bone-regeneration material. Therefore, it is an advantage that no chemical bond is generated between β-TCP and PLGA resin.

Although β-TCP fine particles are not bonded to molecules of PLGA during the process of kneading the PLGA resin and the β-TCP fine particles, PLGA resin can completely cover the surroundings of β-TCP fine particles. It is considered that because of that reason, β-TCP fine particles are not separated from the PLGA resin in drops during the formation of fiber.

(2) Cooling and Solidification of Composite

The composite prepared as described above is collected from the kneader and cooled at normal temperature and solidified. It is considered that when the temperature reaches the crystallization temperature Tc of PLGA (Tc of PLLGA is about 130° C.) during the process of cooling the heated composite, the TCP fine particles dispersed in the composite serve as a crystal nucleating agent and crystal growth of the PLLGA resin is started therefrom.

Because kneading a softened PLGA resin and β-TCP fine particles and applying thermal and mechanical energy in a kneader to disperse the TCP fine particles increases ends of PLGA molecules during the process and forms a large number of nuclear sites, crystals of the PLGA resin is considered to grow from the large number of nuclear sites during the process of cooling the composite. However, because PLGA is a block copolymer, and particularly PDLGA is highly amorphous, speed of crystallization is slow. Therefore it is considered that even with a large number of nuclear sites formed through kneading, crystals do not grow well from the nuclear of TCP fine particles.

(3) Dissolution of Composite with Solvent

The composite produced as described above is immersed in a solvent and the composite is dissolved by stirring to produce a spinning solution. In order to prepare a spinning solution for electrospinning, it is necessary to substantially completely dissolve the composite in the solvent. For that purpose, the composite is preferably stirred in the solvent for 4 hours or more using a magnetic stirrer.

As a solvent to be used in the present invention, chloroform may be used preferably in that solubility in biodegradable resin is good and the solvent can be effectively evaporated from fiber during the process of electrospinning.

The resin concentration dissolved in the solvent in the spinning solution can be selected and adjusted appropriately as needed, but 8% by weight to 10% by weight is preferable for the spinning by electrospinning.

When dissolved in the solvent, molecular chains of the PLGA resin are loosened, which results in the elimination of binding force between the molecular chains, and dispersed separately, which provides a degree of freedom to the molecular chains that were arranged. Subsequently, the molecules of the biodegradable resin in the biodegradable fiber from which the solvent was removed by electrospinning are considered to be rearranged during the course of solidification of the fiber.

<Electrospinning>

A biodegradable fiber is produced by electrospinning by filling a syringe of an electrospinning device with the spinning solution prepared as described above and applying electric charges to a nozzle to eject the spinning solution in a fiber form from the nozzle by a predetermined method and/or under certain conditions.

As the electrospinning process of the present invention, dry-jet-wet-electrospinning may be used preferably. In dry-jet-wet-electrospinning, the fiber that has been ejected from a nozzle into air and solidified by the evaporation of the solvent during the flight enters through the surface of liquid ethanol in the collector tank, sinks in the liquid, and is deposited in a cottonwool-like form in the collector tank. The biodegradable resin is dissolved in chloroform and becomes a content of ES spinning solution, but the resin is not soluble to ethanol contained in a collector tank, and therefore the fiber is deposited in the liquid phase. Dry-jet-wet-electrospinning is disclosed in detail in Study on the Morphologies and Formational Mechanism of Poly(hydroxybutyrate-co-hydroxyvalerate) Ultrafine Fibers by Dry-Jet-Wet-Electrospinning, Shuqi et al. Journal of Nanomaterials Volume 2012 Hindwi Publishing Corporation October 2012, Japanese Patent Laid-Open No. 2012-161363, and U.S. Pat. No. 8,853,298.

Figure 3:
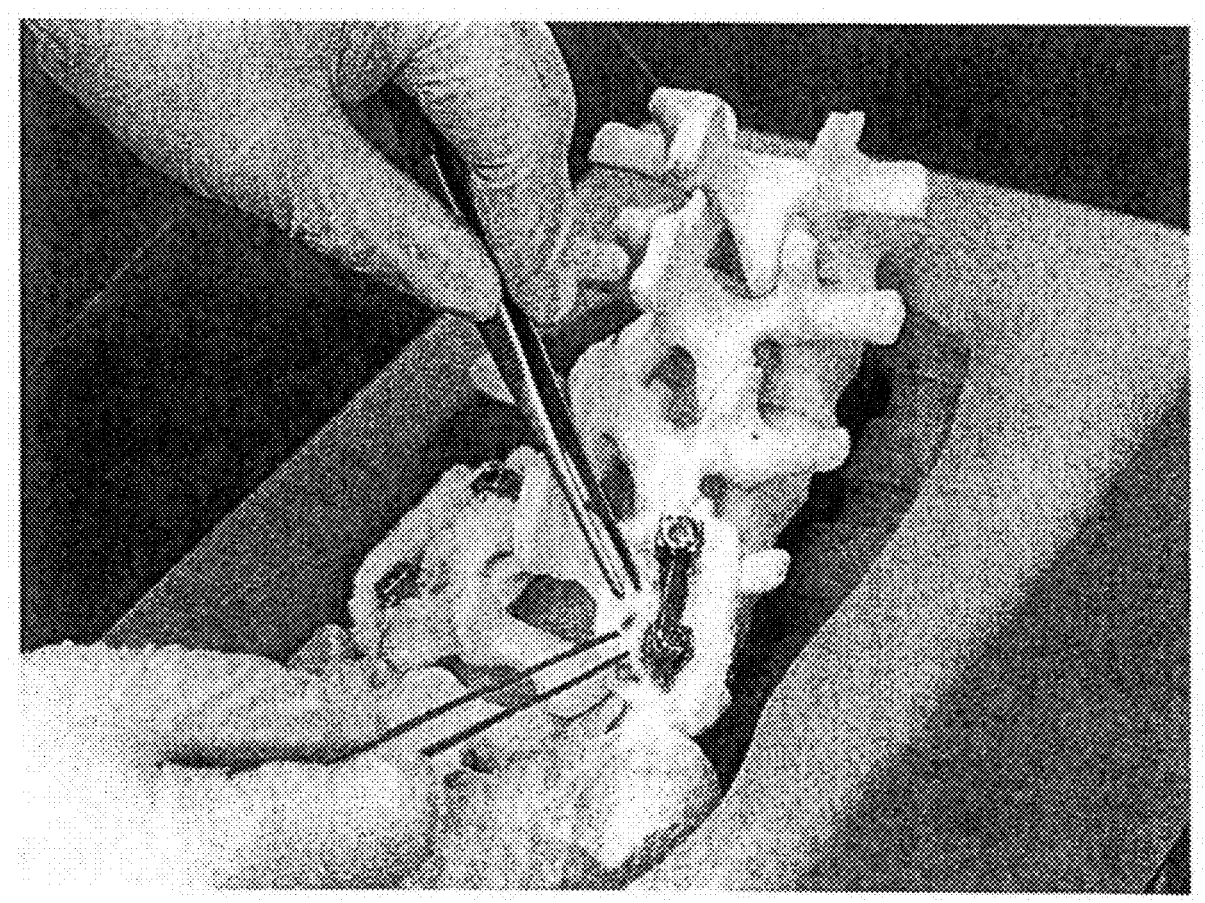
FIG. 3 illustrates a method of using a cottonwool-like form bone regeneration material that is an embodiment of the present invention as a filling placed around an implant device for spinal fusion in the human body.
Figure 5:
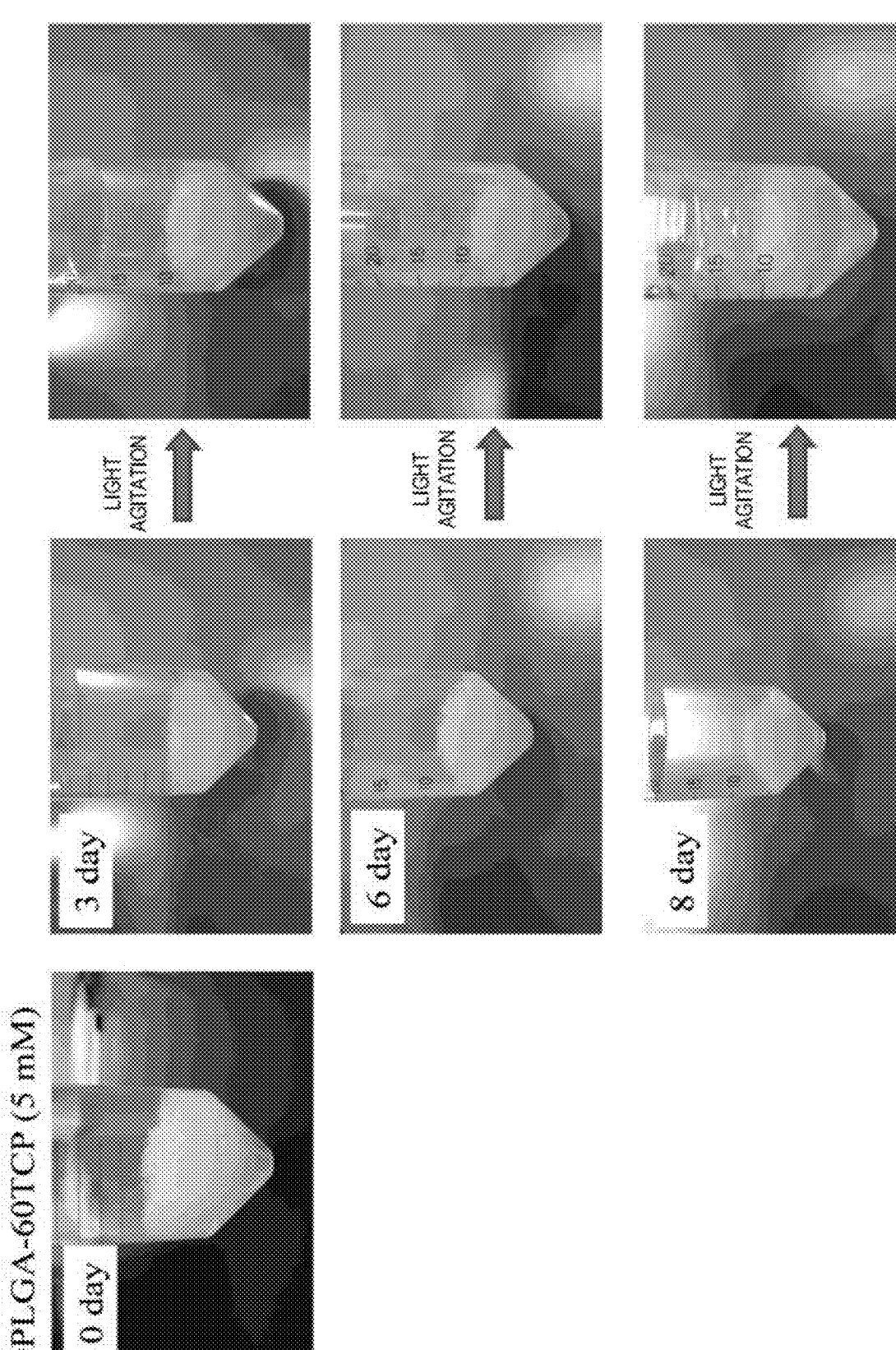
FIG. 5(A) is a photograph illustrating a change in appearance of Sample (1) immersed in a solution of sodium hydroxide for 0 to 8 days.
FIG. 5(B) is a photograph illustrating a change in appearance of Sample (2) immersed in a solution of sodium hydroxide for 0 to 8 days.
FIG. 5(C) is a photograph illustrating a change in appearance of Sample (3) immersed in a solution of sodium hydroxide for 0 to 8 days.
FIG. 5(D) is a photograph illustrating a change in appearance of Sample (4) immersed in a solution of sodium hydroxide for 0 to 8 days.
FIG. 5(E) is a photograph illustrating a change in appearance of Sample (5) immersed in a solution of sodium hydroxide for 0 to 8 days.
Figure 5C:
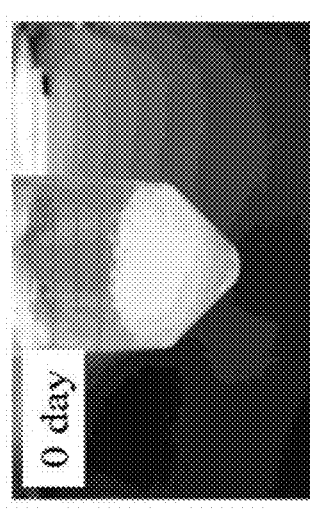
Figure 5:
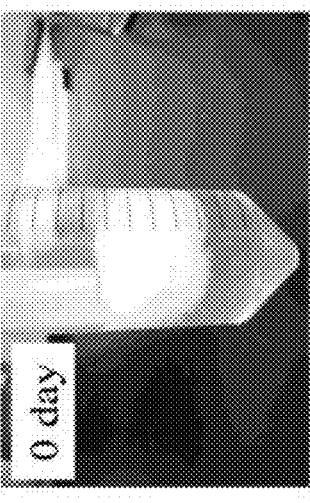

In the present invention, the fiber ejected from a nozzle is sunk in a collector container filled with liquid ethanol and is deposited on a plate of the collector container. Chloroform is removed from the surface of the biodegradable fiber in the liquid ethanol. As a result, the fibers deposited on the collector plate are prevented from adhering to each other and a fluffy cottonwool-like product as illustrated in FIG. 1 can be obtained. The cottonwool-like bone-regeneration material including the biodegradable fiber of the present invention has a bulk density of about 0.001 to 0.1 g/cm³, preferably 0.01 to 0.1 g/cm³, or more preferably 0.01 to 0.04 g/cm³. FIG. 3 illustrates use of the bone-regeneration material of the present invention. The bone-regeneration material of the present invention is superior in ease of handling since it has a fiber with an outer diameter in the range of 10 to 150 μm and a cottonwool-like form with a bulk density in the range described above.

If the PLGA resin is PDLGA, then the fiber deposited in the collector becomes soft and fibers are adhered to each other by chloroform slightly remaining on the surface of the produced fiber and therefore the fiber fails to maintain the form of separate fibers. As a result, it tends to become difficult to collect the fiber deposited in liquid ethanol in the collector container in a cottonwool-like form. For solving this problem to collect the PLGA fiber from the collector in a cottonwool-like form, it is desirable to dry the fiber as soon as possible and remove chloroform from the surface of the fiber.

<Biodegradable Fiber>

Figure 2:
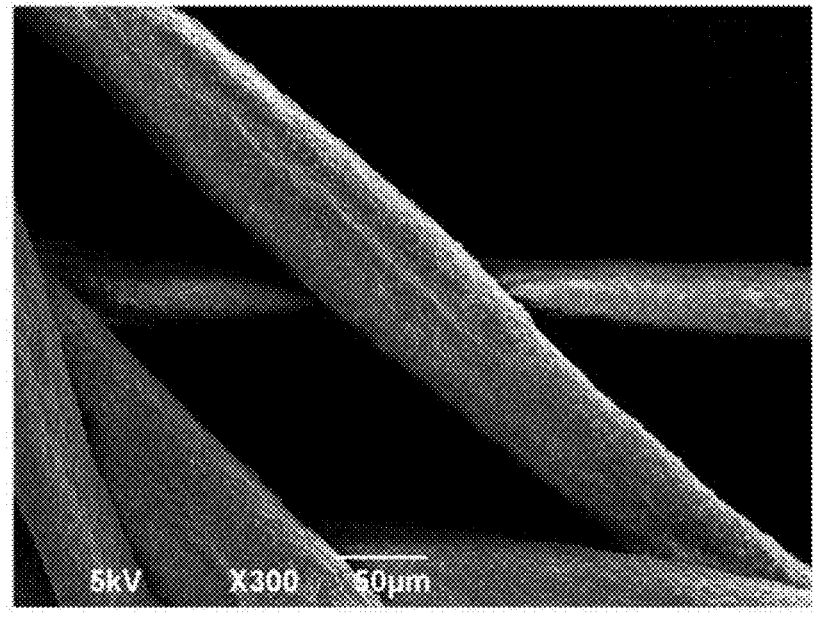
FIG. 2 is an SEM photograph showing the surface of fiber of a bone regeneration material that is an embodiment of the present invention.

FIG. 2 and FIG. 4 illustrate photographs of the appearance of the biodegradable fiber in the bone-regeneration material produced by the electrospinning of the present invention. The outer diameter of the fibers is uneven and ranges from about 10 to 150 μm, but the preferable mean diameter is 10 to 50 μm. Fibers produced by electrospinning tend to have an outer diameter equal to or less than several micrometers. The biodegradable fiber for the bone regeneration material of the present invention is thicker than such fibers. By preparing the fiber with an outer diameter equal to or more than 10 μm, it is possible to create a space (gap) between fibers necessary for cells to enter the inside of the cottonwool-like porous product of the present invention.

The bone-regeneration material made of the biodegradable fiber of the present invention is hydrolyzed at a high speed, starts to be degraded immediately after being implanted in the human body, and then absorbed in the body within several months and disappear.

A numerous number of ultramicropores are formed on the fiber surface of the biodegradable fiber in the bone-regeneration material of the present invention. In the spinning by electrospinning, micropore is formed on the fiber surface in the process of evaporation of the spinning solution ejected in a fiber form from the nozzle. In the bone-regeneration material of the present invention, the area of the interface between the ceramic particles (bone morphogenetic factor) contained and the body fluid is increased markedly by the formation of ultramicropores on the biodegradable fiber and high osteogenic potential is obtained as a result.

<Sterilization Treatment>

The bone-regeneration material of the present invention is preferably sterilized after it is formed in a cottonwool-like form by electrospinning, divided into aliquots in a desired size/weight using tweezers, and wrapped with aluminum. Examples of the sterilization include radiation sterilization (gamma ray, electron beam), ethylene oxide gas sterilization, autoclave sterilization, and the like. The radiation sterilization with gamma ray is preferably used in the present invention.

Experiment 1

1) Outline of Experiment 1

For PLLGA and PDLGA, PLLGA composite samples (1) to (4) and PDLGA composite samples (5) to (7) were prepared with different blending ratios of resin and β-TCP fine particles and conditions of kneading. Spinning was conducted by dissolving the prepared composites in chloroform to prepare spinning solutions for electrospinning.

(I) Kneading of PLLGA

A PLLA/PGA copolymer (PLLGA 85:15) was provided to a kneader with β-TCP fine particles, the mixture was heated at 180° ° C. and kneaded to prepare a composite containing 30% by weight of PLLGA and 70% by weight of TCP fine particles, and the composite was dissolved in chloroform to prepare Spinning solution sample (1).

A PLLA/PGA copolymer (PLLGA 85:15) was provided to a kneader with β-TCP fine particles, the mixture was kneaded at 165° C. to prepare a composite containing 30% by weight of PLLGA and 70% by weight of TCP fine particles, and the composite was dissolved in chloroform to prepare Spinning solution sample (2).

A PLLA/PGA copolymer (PLLGA 85:15) was provided to a kneader with β-TCP fine particles, the mixture was kneaded at 115° C. to prepare a composite containing 30% by weight of PLLGA and 70% by weight of TCP fine particles, and the composite was dissolved in chloroform to prepare Spinning solution sample (3).

A PLLA/PGA copolymer (PLLGA 85:15) was provided to a kneader with β-TCP fine particles, the mixture was kneaded at 165° C. to prepare a composite containing 50% by weight of PLLGA and 50% by weight of TCP fine particles, and the composite was dissolved in chloroform to prepare Spinning solution sample (4).

(II) Kneading of PDLGA

A PDLA/PGA copolymer (PDLGA 85:15) was provided to a kneader with β-TCP fine particles, the mixture was kneaded at 180° C. to prepare a composite containing 30% by weight of PLLGA and 70% by weight of TCP fine particles, and the composite was dissolved in chloroform to prepare Spinning solution sample (5).

A PDLA/PGA copolymer (PLLGA 85:15) was provided to a kneader with β-TCP fine particles, the mixture was kneaded at 165° ° C. to prepare a composite containing 30% by weight of PDLGA and 70% by weight of TCP fine particles, and the composite was dissolved in chloroform to prepare Spinning solution sample (6).

A PLLA/PGA copolymer (PLLGA 85:15) was provided to a kneader with β-TCP fine particles, the mixture was kneaded at 165° C. to prepare a composite containing 50% by weight of PDLGA and 50% by weight of TCP fine particles, and the composite was dissolved in chloroform to prepare Spinning solution sample (7).

(III) Non-Kneaded PLLGA (Comparative Experiment 1)

A PLLA/PGA copolymer (PLLGA 85:15) was provided with β-TCP fine particles to a container filled with chloroform, the mixture was stirred with a stirrer for about 4 hours to prepare a composite containing 30% by weight of PLLGA and 70% by weight of TCP fine particles, and the composite was dissolved in chloroform to prepare Spinning solution sample (8).

(IV) Melt-Kneading of PLLA (Comparative Experiment 2)

30 wt % of PLLA was provided to a kneader with 70% by weight of β-TCP fine particles and the mixture was heated at 185° C. to 190° C. and kneaded while PLLA was melted to prepare a composite of PLA and β-TCP fine particles.

<Materials Used for Sample Preparation>

β-TCP ($Ca_3(PO_4)_2$): β-TCP-100 from Taihei Chemical Industrial Co. Ltd. was used. The product having a particle size of 1.7 mm was crushed to particles with a particle size of about 4 μm (β-TCP crushed product) and used.

PLGA: LG855S produced by Evonik Industries AG was used as PLLGA.

PDLG8531 produced by Purac was used as PDLGA.

<Conditions for Sample Preparation>

Kneader conditions

Kneader: Bench-top kneader PBV-0.1 (batch-type vacuum double arm kneader from Irie Shokai Co., Ltd.) was used.

ES conditions

ES apparatus: NANON (from MECC Co., Ltd.)

Solvent: Chloroform

Resin concentration in solvent: 8 to 10% by weight

Extruder speed: 15 ml/h

The needle size was 18G, the voltage was 25 kV, and the flying distances from the nozzle to the collector was 25 cm. The collector container was filled with liquid ethanol in which the fiber produced by electrospinning was received and deposited.

2) Results of Experiment 1

Results of Experiment 1 are illustrated in FIG. 4(A) and (2).

By kneading PLLGA and β-TCP fine particles in the kneader at a heating temperature of 165° C., PLLGA and β-TCP fine particles were able to be kneaded by applying thermal and mechanical energy within the work viscosity range. Kneading at a higher heating temperature of the kneader of 185° C. resulted in too low viscosity of PLLGA and unsatisfactory mixing of the β-TCP fine particles powder with the PLLGA resin, leaving some powder unmixed. Contrary, kneading at a lower heating temperature of the kneader of 115° C. resulted in too high viscosity of PLLGA and made it difficult to mix the β-TCP fine particles powder and the PLLGA resin in the kneader.

The viscosity of PDLGA is more easily decreased by heating as compared with PLLGA and kneading with heating at 165° C. tends to result in adhesion of resin onto the blades of the kneader, leaving powder incompletely mixed and small portions unmixed. By elongating the time of kneading the polymer and the powder together for about 3 minutes to mix the powder with the resin at the same heating temperature, it was somehow possible to mix them. However, the fiber obtained by dissolving the composite prepared thereby in chloroform and spinning the resultant solution by ES was soft and thus could be hardly formed into a cotton-wool-like form after drying.

In Comparative experiment 1, it was possible to prepare a solution in which the β-TCP fine particles are dispersed in a solution of chloroform/resin to the state in which particles of the powder were not visible in visual observation by stirring PLLGA and the β-TCP fine particles for about 4 hours in a container filled with chloroform without kneading them in a kneader. However, attempt to spin the solution by charging the solution as a spinning solution into a syringe of an electrospinning apparatus and applying the voltage to the solution did not result in spinning by the Taylor corn phenomenon but the spinning solution was extruded from the nozzle, dropped downward, and deposited in a thick fiber form.

In Comparative experiment 2, providing PLLA (melting point: 180° C.) and powder of the β-TCP fine particles at a ratio of 30% by weight/70% by weight to a kneader and heating the mixture at a set temperature of 185° C. to 190° C. melted PLLA into a liquid phase state. Rotating the blades of the kneader in the state to knead the mixture was associated with adhesion of the melted PLLA resin onto the inner wall surface of the kneader, leaving the powder of β-TCP fine particles incompletely mixed with the PLLA resin and some portions as a white powder.

3) Analysis and Evaluation of Results of Experiment 1

The method for preparing a composite by first softening a PLGA resin within a working viscosity range, then mixing the PLGA resin with powder of β-TCP fine particles, and kneading the mixture with applying force in a heated kneader was found to be extremely effective in preparing a composite in which the powder of β-TCP fine particles is dispersion and mixed in PLGA. Dissolving the composite in chloroform and electrospinning the resultant solution as a spinning solution was successful in producing fiber substantially stably.

On the contrary, when a viscosity range of the PLGA resin was higher or lower than the working viscosity range upon kneading it, it was not easy to disperse powder in the PLGA resin, making it difficult to prepare a composite and as a result to dissolve the composite with a solvent and spin the solution by an electrospinning process.

When PLA, which is a crystalline resin, was heated at a temperature equal to or higher than the melting point to have the resin in a molten condition, the viscosity of the resin is rapidly decreased so that viscosity of the resin became lower than a working viscosity range, which, as a result, made it difficult to knead the resultant mixture by applying force and to completely mix the powder with the resin by kneading.

PDLGA may not be easily molded and processed because it is more amorphous than PLLGA. But use of the method of the present invention made it possible to produce fiber with containing a large amount of β-TCP fine particles in PDLGA resin by electrospinning. However, the produced PDLGA fiber was soft and fibers tend to adhere to each other by chloroform slightly remained on the surface of the fiber. Therefore, it is possible to deposit the PDLGA fiber in a cottonwool-like form in liquid ethanol. However, after it is taken out from the liquid ethanol, it is difficult to maintain an independent fiber form. To collect the biodegradable fiber in a cottonwool-like form from the collector, it is necessary to remove chloroform from the fiber and dry the fiber as soon as possible.

Experiment 2

1) Outline of Experiment 2

Samples (1) to (6) of the biodegradable fiber including PLGA and β-TCP were prepared, and each sample was measured for crystallinity of PLGA, shape decay in an aqueous solution, and NMR measurement.

(1) 70 β-TCP-30 PLLGA (85:15)

(2) 60 β-TCP-40 PLLGA (85:15)

(3) 50 β-TCP-50 PLLGA (85:15)

(4) 100 PLLGA (85:15)

(5) 70 β-TCP-30 PDLGA (85:15)

(6) 50 β-TCP-50 PDLGA (85:15)

<Materials Used for Sample Preparation>

β-TCP (Ca$_3$(PO$_4$)$_2$): β-TCP-100 from Taihei Chemical Industrial Co. Ltd. was used. The product having a particle size of 1.7 mm was crushed to particles with a particle size of about 4 μm (β-TCP crushed product) and used.

PLGA: LG855S produced by Evonik Industries AG was used as PLLGA (85:15).

PDLG8531 produced by Purac was used as PDLGA (85:15).

<Conditions for Sample Preparation>

Kneader conditions

Kneader: Bench-top kneader PBV-0.1 (from Irie Shokai Co., Ltd.).

Temperature: 160° ° C.

Time: Polymer alone was kneaded for 3 and half minutes and then TCP was added and the mixture was kneaded for 11 minutes: in total for 14 and half minutes. For (6) 50 TCP-50 PLGA (PDLGA 85:15), the polymer and TCP were provided to a kneader at the same time and kneaded for 14 and half minutes.

ES Conditions

ES apparatus: NANON (from MECC Co., Ltd.)

Solvent: Chloroform

Resin concentration in solvent: 8% by weight for (1) to (4), 16% by weight for (5), and 12% by weight for (6).

Voltage: 20 kV for (1) to (4), 28 kV for (5), and 25 kV for (6).

Extruder Speed: 15 ml/h

The needle size was 18G, the voltage was 20 to 28 kV, and the flying distances from the nozzle to the collector was 25 cm. The collector container was filled with liquid ethanol in which the fiber spined by electrospinning was received and deposited.

<DSC Measurement>

The crystallinity of samples of (1) to (6) was measured by DSC.

<NMR Measurement>

Whether coordination was formed between carboxyl groups in PLGA and calcium ions in TCP in the samples of (1) and (4) was examined by NMR.

<Observation of Shape Decay in Aqueous Solution>

Samples of (1) to (5) were immersed in an aqueous solution of sodium hydroxide and evaluated for shape decay of the cottonwool-like samples after a predetermined immersion time.

Solution: 5 mmol/L aqueous solution of sodium hydroxide

Immersion time: 0, 3, 6 and 8 days

Sample weight: 100 mg each

Volume of solution: 20 ml

Leave at room temperature

Agitate by inverting the container in the morning and in the evening.

Photographs were taken just after the immersion and at suitable time points after the immersion and the change of the appearance was observed.

2) Results of Experiment 2

<DSC Measurement>

The results are illustrated in FIGS. 6(A) and 6(B).

<NMR Measurement>

Results are illustrated in FIGS. 7(A) and 7(B).

<Shape Decay Observation in Aqueous Solution>

The results are illustrated in FIGS. 5(A) to 5(E).

Sample (1) (30 PLLGA-70 TCP) was immersed in an aqueous solution of sodium hydroxide for an immersion period of 0, 3, 6 and 8 days and the change of the appearance was observed. As a result, 6 days after the start of immersion, the apparent volume of the cottonwool-like sample was decreased to about two-thirds and light agitation caused dispersion of a large number of short fibers in the container. 8 days after the start of immersion, the apparent volume of the cottonwool-like sample was decreases to about one-thirds and light agitation caused dispersion of short fibers throughout the container.

Sample (2) (40 PLLGA-60 TCP) was immersed in an aqueous solution of sodium hydroxide for an immersion period of 0, 3, 6 and 8 days and the change was observed. As a result, a phenomenon approximately similar to that of Sample (1) was observed, but the decrease in apparent volume of the cottonwool-like sample after the start of immersion was slower than that of Sample (1) and a less amount of short fibers were dispersed in the container than that of Sample (1) when agitated lightly.

Sample (3) (50 PLLGA-50 TCP) was immersed in an aqueous solution of sodium hydroxide for an immersion period of 0, 3, 6 and 8 days and the change was observed. As a result, a phenomenon approximately similar to those of Samples (1) and (2) was observed, but the decrease in apparent volume of the cottonwool-like sample after the start of immersion was even slower than that of Sample (2) and an even less amount of short fibers were dispersed in the container than that of Sample (2) when agitated lightly.

Sample (4) (100 PLLGA) was immersed in an aqueous solution of sodium hydroxide for an immersion period of 0, 3, 6 and 8 days and the change was observed. As a result, 8 days after the start of immersion, the apparent volume of the cottonwool-like sample was found to be slightly decreased and dispersion of short fibers in the container when agitated lightly was also in a little amount.

Sample (5) (30 PDLGA-70 TCP) was immersed in an aqueous solution of sodium hydroxide for an immersion period of 0, 3, 6 and 8 days and the change was observed. As a result, 3 days after the start of immersion, the cotton-wool-like appearance was almost lost and light agitation caused dispersion of short fibers throughout the container. This phenomenon was intensified progressively 6 and 8 days after the start of immersion.

3) Analysis and Evaluation of Experimental Results (i) Differential Scanning Calorimetry (DSC) Measurement In PLLGA/TCP, the crystallinity of the samples was lower as the content of PLLGA was lower and the content of TCP was higher. The sample of PLLGA 100%, which did not contain β-TCP, had a considerably higher crystallinity than the samples that contained TCP.

(ii) Disintegration Measurement

In the samples of PLLGA/TCP, the hydrolysis rate was higher as the PLLGA content was lower and the β-TCP content was higher. This result is presumed to indicate that the hydrolysis rate of the sample is higher as the crystallinity of PLLGA is lower.

(iii) NMR measurement

13C CP/MAS-NMR spectra of PLGA (100) and TCP/PLGA (70-30) were measured.

Phases around the carbonyl group (C=O; ~170 ppm) were enlarged together and the peak fitting was conducted.

Although it is hard to see because of many noises, from both PLGA (100) and TCP/PLGA (70-30), a wide peak indicated with a dashed line and a peak indicated with a dashed line having a top at 170.4 ppm were possible to be separated (Gaussian). There was no peak shifted in the magnetic field for either of the samples. Therefore, it can be considered that no Ca2+ ion is coordinated to any of the carboxyl-groups (although it is not sure, but a separated peak in a dashed line may be due to fluctuations due to the high amorphous nature).

Although PLGA including lactic acid and glycolic acid at a ratio of 85 to 15 was used as a biodegradable resin in Examples of the present application, the ratio of lactic acid and glycolic acid is not limited thereto and includes 75 to 25 and 50 to 50. It is considered that the higher the percentage of glycolic acid, the more amorphous the PLGA is and the higher the hydrolysis rate of the biodegradable fiber using it is.

The bone-regeneration material produced using the method of the present invention may be used singly as well as by a method involving filling a bone defect with an autologous bone wrapped with the cottonwool-like material. The bone regeneration material of the present invention is used to fill a defect and helps the bone formation in that state because of a high affinity with the autologous bone. FIG. 3 illustrates use of an autologous bone wrapped with the bone regeneration material of the present invention.

Since the bone-regeneration material produced using the method of the present invention has β-TCP fine particles uniformly dispersed in a biodegradable fiber, the degradation and absorption of PLGA and bone replacement of β-TCP are thought to occur continuously in parallel at the same time.

What is claimed is:

1. A bone-regeneration material comprising a biodegradable fiber produced using an electrospinning process,
    wherein the biodegradable fiber comprises 30 to 50 wt % of a copolymer of poly-L-lactic acid and polyglycolic acid (PLLGA) resin and 70 to 50 wt % of phase tricalcium phosphate (β-TCP) fine particles substantially uniformly dispersed in the PLLGA resin without forming aggregates,
    wherein the β-TCP fine particles are not chemically bonded to the PLLGA resin, and surroundings of the β-TCP fine particles are covered by the PLLGA resin so that the β-TCP fine particles are not separated from the biodegradable fiber during a formation of the fiber, and
    wherein the bone-regeneration material is has been sterilized by gamma radiation.

2. The bone-regeneration material of claim 1, wherein a weight ratio of lactic acid and glycolic acid in the PLLGA resin is approximately 85-50:15-50.

3. The bone-regeneration material of claim 1, wherein outer diameters of the β-TCP fine particles are in a range of 0.5 µm to 4 µm.

4. The bone-regeneration material of claim 1, wherein an outer diameter of the biodegradable fiber is 10 µm to 250 µm.

5. The bone-regeneration material of claim 1, wherein the bone-regeneration material formed of the biodegradable fiber is in a cotton-wool form having a bulk density of 0.01 to 0.1 g/cm³.

6. The bone-regeneration material of claim 1, wherein a molecular weight of the PLLGA resin is 60,000 to 600,000.

* * * * *